United States Patent [19]
Edrich et al.

[11] Patent Number: 5,476,438
[45] Date of Patent: Dec. 19, 1995

[54] METHOD AND APPARATUS FOR NEUROMAGNETIC STIMULATION

[75] Inventors: Jochen Edrich; Tongsheng Zhang, both of Neu-Ulm, Germany

[73] Assignee: Zentralinstitut fur Biomedizinische Technik Universitat Ulm, Ulm, Germany

[21] Appl. No.: 212,035

[22] Filed: Mar. 11, 1994

[30] Foreign Application Priority Data

Mar. 11, 1993 [DE] Germany .......................... 43 07 767.6

[51] Int. Cl.$^6$ ................................ A61B 8/00; A61N 2/04
[52] U.S. Cl. ................................ 600/2; 600/13; 600/14; 600/15
[58] Field of Search ...................... 600/2, 9–15; 607/156

[56] References Cited

PUBLICATIONS

D. Cohen and N. B. Cuffin, Developing a More Focal Stimulator, Journal of Clinical Neurophysiology, 1991, pp. 102–120.
S. N. Erné and J. Edrich, Designing Multichannel Sensor Arrays for Biomagnetism, Proc. IEEE–EMS Conference Paris, CH3207, 1992, pp. 1772–1773.
B. A. Evans, Magnetic Stimulation of the Peripheral Nervous System, Journal of Clinical Neurophysiology, 1991, pp. 77–84.
A. T. Barker, An Introduction to the Basic Principles of Magnetic Nerve Stimulation, Journal of Clinical Neurophysiology, 1991, pp. 26–37.
L. A. Frizzell, Threshold Dosages for Damage to Mammalian Liver by High Intensity Focused Ultrasound, IEEE Trans. Biomed. Eng. 24, 1988, pp. 578–581.
J. A. Evans and M. B. Tavakoli, Ultrasonic Attenuation and Velocity in Bone, Phys. Med. Biol. vol. 35, S. 1990, No. 10, pp. 1387–1396.
Umemura and C. A. Cain, Acoustical Evaluation of a Prototype Sector–vortex Phased–array Applicator, IEEE Trans. on Ultrasonics, Ferroeletrics and Frequency Control, vol. 39, 1992, No. 1, pp. 32–38.

*Primary Examiner*—Angela D. Sykes
*Assistant Examiner*—Stephen Huane
*Attorney, Agent, or Firm*—Dorr, Carson, Sloan & Birney

[57] ABSTRACT

A method for neuromagnetic stimulation or functional neuromuscular stimulation comprises applying a magnetic field with a magnetic induction B to a subcutaneous nerve tissue to be stimulated, and simultaneously directing a focused beam of ultrasonic waves into the magnetic field region such that the ultrasonic waves vibrate orthogonally to the direction of the magnetic field, thereby producing a subcutaneous focus of stimulation having a focal diameter of approximately 1 cm, in order to confine the stimulation into a single nerve bundle or one single nerve region, and to avoid unintentional stimulation of adjoining nerve regions. An apparatus is described for carrying out such method.

15 Claims, 2 Drawing Sheets

METHOD AND APPARATUS FOR NEUROMAGNETIC STIMULATION

FIELD OF THE INVENTION

The invention is concerned with a method and apparatus for functional neuromuscular and neuromagnetic stimulation, respectively, of nerves by the application of a magnetic field to the subcutaneous tissue containing the nerves to be stimulated.

PRIOR ART

There have been recent developments in neuromagnetic and functional neuromuscular stimulation, particularly in the field of non-contacting magnetic stimulation. Such stimulation is applied in research and clinical applications, for example, in neurology, rehabilitation medicine, and non-invasive functional stimulation of central and peripheral nerves. Representative publications on such developments are: D. Cohen and N. B. Cuffin, Developing a More Focal Stimulator, Journal of Clinical Neurophysiology, 1991, pg. 102–120; S. N. Erné and J. Edrich, Designing Multichannel Sensor Arrays for Biomagnetism, Proc. IEEE-EMBS Conference Paris, CH3207, 1992, pg. 1772/1773; B. A. Evans, Magnetic Stimulation of the Peripheral Nervous System, Journal of Clinical Neurophysiology, 1991, pg. 77–84; and A. T. Barker, An Introduction to the Basic Principles of Magnetic Nerve Stimulation, Journal of Clinical Neurophysiology, 1991, pg. 26–37.

The efficiency and specificity of these methods are very limited because the magnetic fields cannot yet be focused into a small volume of less than one (1) cubic centimeter, which is important for various reasons. Precise focusing of relatively strong fields of approximately one (1) tesla into a single nerve bundle or into one central nerve region, such as the motor area of the thumb in the precentral cortex region, is required; otherwise, the adjacent area, e.g., that of the index finger, which is located within a distance of about 1 cm, would also be stimulated unintentionally.

The application of ultrasound and means therefore were investigated by L. A. Frizzell, Threshold Dosages by High Intensity Focused Ultrasound, IEEE Trans. Biomed, Eng. 24, 1988, pgs. 578–581; J. A. Evans and M. B. Tavakoli, Ultrasonic Attenuation and Velocity in Bone, Phys. Med. Biol. Vol. 35, 1990, No. 10; and S. Umemura and C. A. Cain, Acoustical Evaluation of a Prototype Sector-vortex Phased-array Applicator, IEEE Trans. on Ultrasonics, Ferroelectrics and Frequency Control, Vol. 39, 1992, No. 1, pg. 32–38.

It is an object of the invention to provide a novel method and apparatus for neuromagnetic stimulation of nerve tissue.

It is a further object of the invention to provide a method and apparatus for neuromagnetic stimulation that avoid the focusing problems of conventional magnetic stimulation.

It is a still further object of the invention to provide a method and apparatus for neuromagnetic stimulation that permits precise stimulation of a restricted subcutaneous region of the tissue.

SUMMARY OF THE INVENTION

The above objects of the present invention are achieved by the novel method and apparatus described hereinafter. The method of the invention for neuromagnetic stimulation provides the steps of applying a magnetic field with a magnetic induction B to the nerve tissue to be stimulated and simultaneously directing a focused beam of ultrasonic waves into the magnetic field region such that the ultrasonic waves vibrate orthogonal to the direction of the magnetic field, thereby producing a subcutaneous focus of stimulation having a focal diameter of approximately 1 cm.

The apparatus according to the invention comprises means for applying a magnetic field with a magnetic induction B to a subcutaneous nerve tissue to be stimulated, and ultrasonic radiation means for simultaneously directing a focused beam of ultrasonic waves into the magnetic field region such that the ultrasonic waves vibrate orthogonal to the direction of the magnetic field, thereby producing a subcutaneous focus of stimulation having a focal diameter of approximately 1 cm.

According to the invention, a magnetic field with magnetic induction B orthogonal to the focused ultrasound wave is simultaneously applied such that the stimulating magnetic field is focused to approximately 1 cm in diameter. The ultrasound can be applied as a single pulse or as a series of pulses. In a preferred embodiment ultrasound frequencies are in the frequency range between 0.2 and 3.0 MHz. Particularly sharp focusing can be achieved in the frequency range of about 0.3 to 0.5 MHz. The magnetic field with induction B can be a DC field or a pulsed field or even a field of a series of pulses.

The method of the invention achieves the unexpected advantage that by the superimposition of focused ultrasound, the relatively large magnetic fields required to be effective can be directed onto a single nerve bundle or a single central nerve region, and unintentional stimulation of adjoining nerve regions is avoided.

The above and other objects and advantages of the invention are achieved in an illustrative embodiment described hereinafter in more detail.

DETAILED DESCRIPTION

Figure 1:
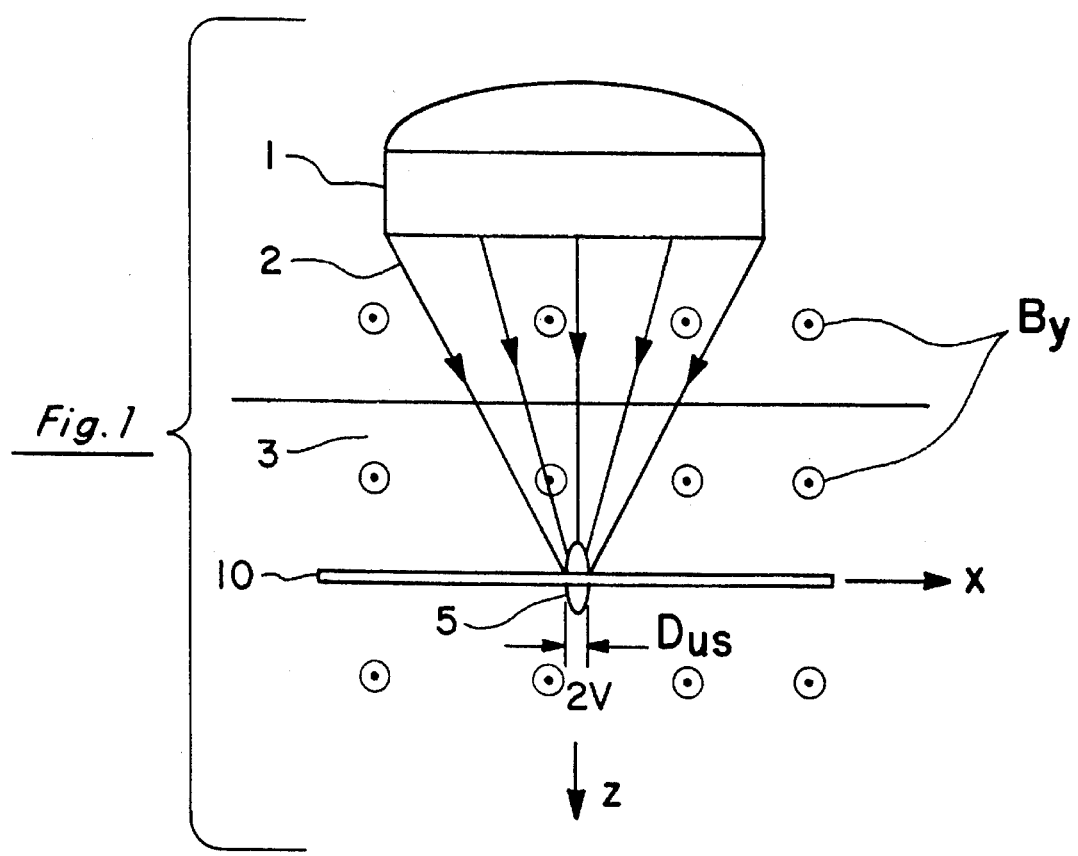
FIG. 1 shows a cross section through an ultrasound source and through nerve tissue.
Figure 2:
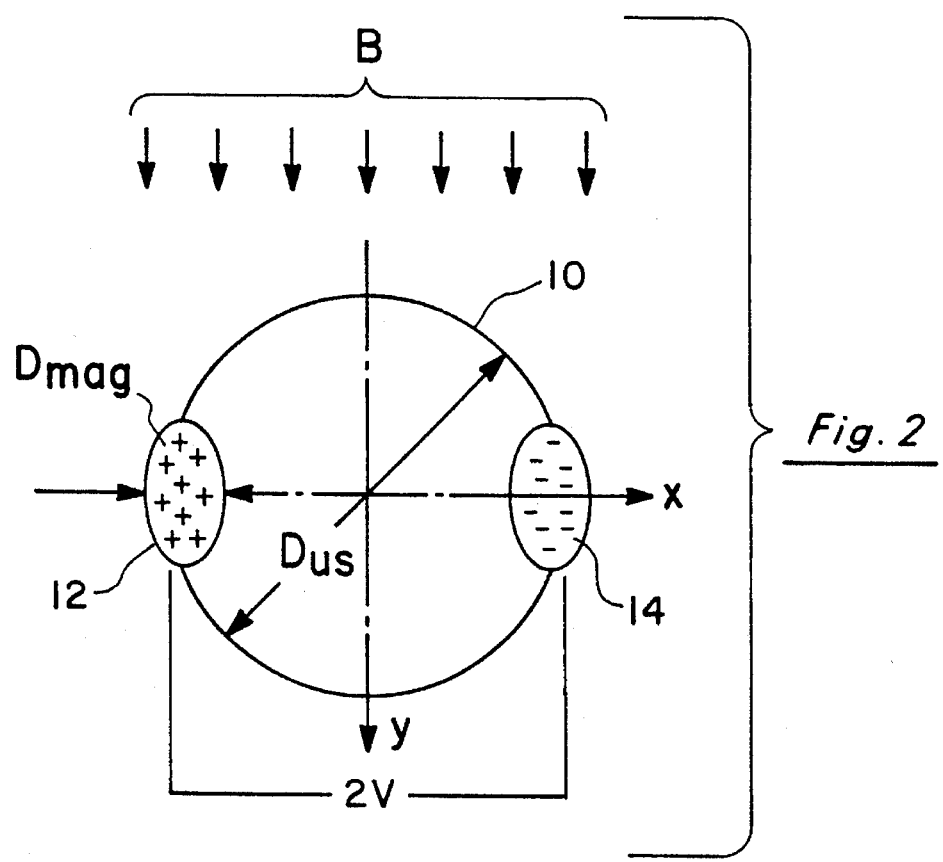
FIG. 2 is the x–y plane of a cross section through the ultrasound focus in the tissue.

Referring to FIG. 1, there is shown an ultrasonic source 1 which emits, using phase and amplitude control, focused ultrasonic waves 2, by an array of ultrasound emitters, focused ultrasonic waves 2 into a subcutaneous region of tissue 3 such that it produces a subcutaneous ultrasound focus (region) 5 approximately 1 cm in diameter orthogonal to the z axis of the main direction of radiation. This can readily be accomplished in the frequency range 0.2 to 3.0 MHz, and is particularly easy in the frequency range of about 0.3 to 0.5 MHz. If the power density $P_{us}$ in the focal region is sufficiently high, the tissue particles vibrate at the ultrasound frequency. Ionized particles within the nerve tissue and, particularly, electrons are therefore mobilized, which corresponds to an alternating current J. Simultaneous application of a magnetic field with an induction B orthogonal to the direction of vibration or current J will produce a so-called lorentzian force F orthogonal to B and J; this B-field can be a DC magnetic field or a pulsed magnetic field. FIG. 2 shows that the simultaneous interaction of a constant B-field and focused ultrasound leads to an accumulation of negative charges in the region x>0, and an equally large accumulation of positive charges in the region $x<0$. The resulting voltage $2V$ between the two charged regions is given by:

$$V = B \cdot D_{us} \cdot U_x \tag{1}$$

where $D_{us}$ is the diameter of the ultrasound focus 5 in the transverse direction, and $U_z$ is the velocity of the charge carriers resulting from the ultrasound. This velocity $U_z$ is related to the power density of the ultrasound, $P_{us}$, the specific tissue density $\rho$, and the ultrasound velocity in tissue, $c_{us}$, by:

$$U_z = \sqrt{2 \times P_{us}/(\rho \times c_{us})} \tag{2}$$

For a numerical estimate the following example is given:

$\rho = 1000$ kg/m$^3$ $c_{us} = 1500$ m/sec $B = 1$ tesla $P_{us} = 2000$ W/cm$^2$ $D_{us} = 0.01$ m $f = 0.5$ MHz Using the two above equations, one can compute the induced voltage:

$$\begin{aligned} V &= B \times D_{us} \times \sqrt{2 \times P_{us}/(\rho \times c_{us})} \\ &= 1\text{ tesla} \times 0.01\text{ m} \times \sqrt{\frac{2 \times 2000\text{ W/cm}^2}{(1000\text{ kg/m}^3) \times 1500\text{ m/sec}}} \\ &= 103\text{ mV}, \end{aligned}$$

which results in a depolarizing nerve stimulation. Here the ultrasound frequency $f_{us}$ is assumed to be 0.5 MHz, and the wavelength is $$\lambda = c_{us}/f_{us} = (1500\text{ m/sec})/0.5 \cdot 10_6\text{ Hz} = 3\text{ mm} \tag{3}$$

In theory it is now possible to obtain focal diameters as low as $$D_{us} \lambda/2 = 1.5\text{ mm} \tag{4}$$

The value $D_{us} = 1$ cm, which was assumed above, can therefore easily be achieved in practice.

The transverse x–y plane 10 shown in FIG. 2 represents the ultrasound focus 5 of FIG. 1. This transverse plane 10, where the ultrasound impinges, shows the concentration region 12 for positive charge carriers which result in the depolarizing stimulation. The concentration region 12 of the positive charge carriers and the diametral concentration region 14 of the negative charge carriers are produced by simultaneous interaction of the focused ultrasound and the magnetic field B.

Applying a series of pulses can increase the effective pulse width of the stimulating voltage, and thus decrease the excitation voltage significantly. The positively charged region in FIG. 2 will have an extension $D_{mag} = 0.4 \cdot D_{us} = 4$ mm in the x direction (3 db points). Even at a depth of many centimeters, this value of $D_{mag}$ still holds for the focusing accuracy, making this accuracy higher by factors than conventional magnetic stimulation accuracy.

In order to increase the focusing accuracy further, amplitude and phase controls can be provided for the ultrasound arrays that are steered by output data from structural anatomic images produced by Computer Aided Tomography (CAT), Magnetic Resonance Imaging (MRI) or diagnostic ultrasound scanning.

The waveforms and relationships of the applied ultrasound and magnetic waves should be properly adjusted to achieve optimum stimulation performance. This can be derived from the induced electric field $E_x$, which follows from the gradient of the voltage V according to equations (1) (2) as:

$$\begin{aligned} E_x &= -\frac{\delta V}{\delta x} \\ &= -B_y \times \sqrt{2P_{us}(x,y,z)/(\rho \times c_{us})} \times \cos(2\pi ft - 2\pi z/\lambda) \end{aligned} \tag{5}$$

where $\lambda$ is the wavelength of the ultrasound in the tissue medium. We can now apply at the same frequency f a sinusoidal magnetic field By:

$$By = Bo \cdot \cos(2\pi ft - \alpha). \tag{6}$$

Combining equations (5) and (6) yields:

$$\begin{aligned} E_x &= -\frac{dV}{dx} \\ &= -B_o \times \sqrt{2P_{us}(x,y,z)/(\rho \times c_{us})}\ \cos(2\pi ft - 2\pi z/\lambda) \times \\ &\quad \cos(2\pi ft - \alpha) \end{aligned} \tag{7}$$

The field $|E_x|$ reaches for:

$$\alpha = \frac{2\pi z_o}{\lambda} + 2n\pi\ (n = \text{integer number}) \tag{8}$$

its maximum value in the vicinity of the focal region ($z = z_o$):

$$\begin{aligned} |E_x|\alpha &= B_o \times \sqrt{2P_{us}(x,y,z)/(\rho \times c_{us})} \times \cos^2(2\pi ft - 2\pi z/\lambda) \\ &= E_{max} \times \cos^2(2\pi ft - 2\pi z/\lambda) \end{aligned} \tag{9}$$

These expressions show that the induced electric field in the synchronized case is a standing wave with a maximum at the focus, and a field value that is larger by a factor of two than that in the unsynchronized case.

Figure 3:
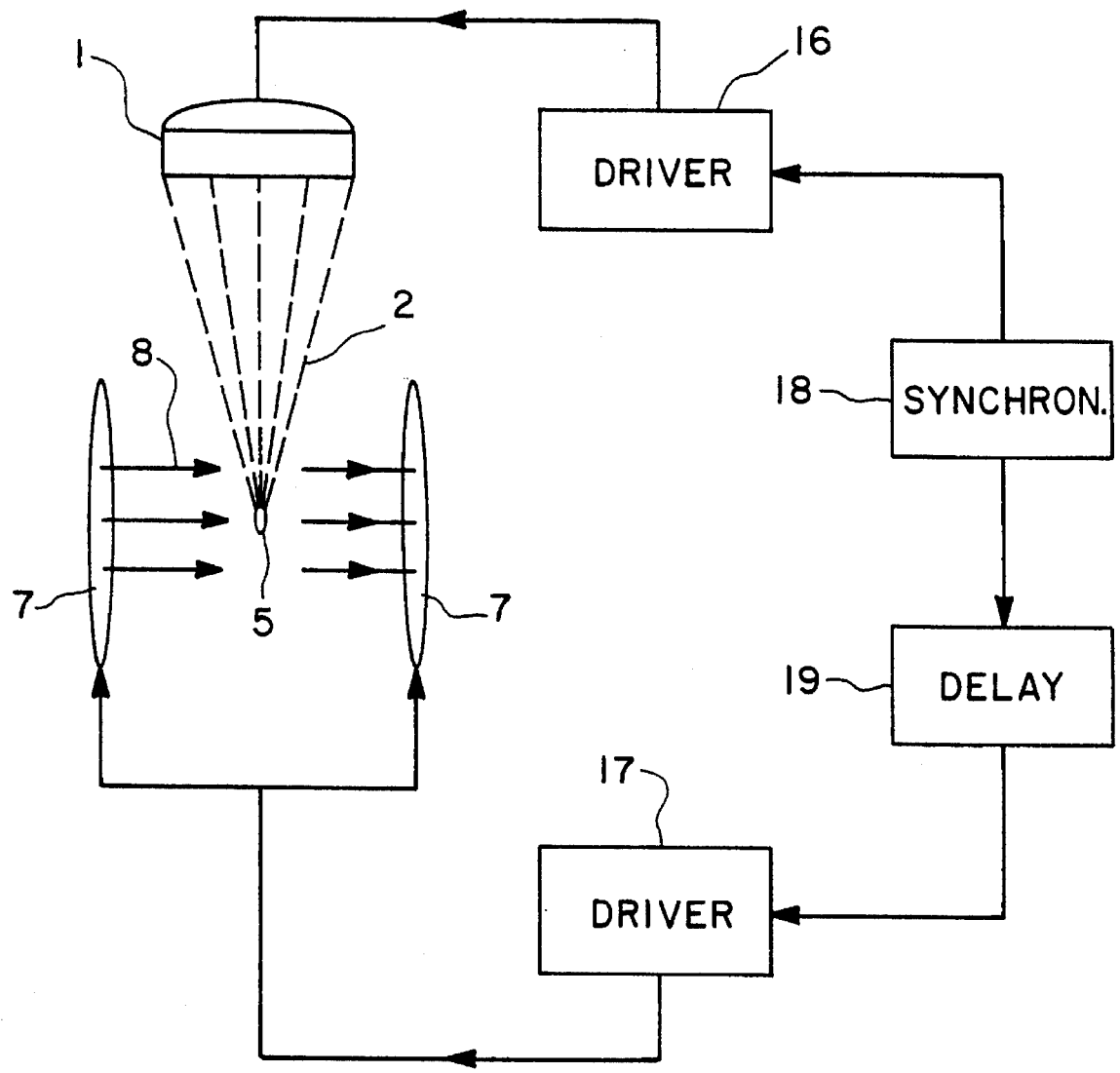
FIG. 3 shows a block diagram of an apparatus implementing the method of the present invention.

FIG. 3 depicts a schematic diagram of a practical setup including the ultrasound source 1, which focuses the ultrasound waves 2 into the focus 5. Coils 7 produce the magnetic fields 8. Both the ultrasound source 1 and the coils 7 are fed by drivers 16 and 17, respectively. A synchronizer 18 and a delay circuit 19 perform the frequency and phase control. To change the stimulating point, one must adjust the delay circuit 19, which results in a high degree of selectivity for this type of stimulation. Instead of two sinusoidal magnetic and ultrasound fields, pulsed fields or field trains can be applied. Again, a maximum for the stimulating E field is achieved by synchronization, i.e., phase and frequency equalization of these two quantities.

When applying this in the clinically important cerebral area, one is confronted with two main problems:

(1) the cranial bone structure attenuates by 10 to 20 dB, (2) unwanted secondary focuses are created by reflections in the intracranial region.

Both of these problems can be solved by the use of several focusing ultrasound systems that enclose the head in a helmet-like fashion. In this way the focal power density can be increased by multiples, without overloading the prefocal region. The above-mentioned amplitude and phase controls, as well as feedback via CAT, MRI or diagnostic ultrasound scanning, can again be utilized to reduce secondary focuses.

Since the focusing is primarily determined by the ultrasound, the magnetic coils can be made relatively large, which facilitates the production of large magnetic fields. In contrast to conventional magnetic stimulation, this will not significantly reduce the focusing accuracy.

To reduce even further the possibility of prefocal field overloading, one can implement multiple-coil systems similar to multichannel systems for magnetoencephalography and magnetocardiography.

The likelihood of unstable cavitation by ultrasound rises with increasing power density of the ultrasound wave. For most body regions the threshold lies above 6000 W/cm$^2$. With a power level of 2000 W/cm$^2$, the method described here lies safely below that threshold.

Heating by focused ultrasound is being applied in oncological hyperthermia. If heat conduction effects are neglected, the resulting time rate of temperature increase dT/dt can be calculated to be:

$$dT/dt = 2\alpha \cdot P_{us}/(\rho \cdot c_m) \quad (10)$$

Assuming typical tissue data (ultrasound absorption coefficient $\alpha=0.015$ cm$^{-1}$ and specific heat $c_m=4.2$ joule/(kg), one obtains, at an ultrasound frequency of 0.5 MHz and an ultrasound pulse width dt= 1 ms, a temperature increase of only 0.014K clearly a negligible amount of heating.

While the present invention has been described in particularity, it is to be understood that changes and modifications could be made by those skilled in the art under the scope of the claims hereinafter.

We claim:

1. A method for neuromagnetic stimulation of a subcutaneous nerve tissue comprising the steps of:

applying a magnetic field to a region with a magnetic induction B directed toward said subcutaneous nerve tissue for stimulation of said subcutaneous nerve tissue, and simultaneously directing a focused beam of ultrasonic waves at a selected frequency into the magnetic field region, said ultrasonic waves vibrating orthogonally to the direction of the magnetic field to produce a subcutaneous focus of stimulation on said subcutaneous nerve tissue, said subcutaneous focus having a focal diameter of approximately 1 cm.

2. The method of claim 1 wherein the frequency of the ultrasonic waves is in a range of 0.2 to 3 MHz.

3. The method of claim 1 wherein the frequency of the ultrasonic waves is in the range of 0.3 to 0.5 MHz.

4. The method of claim 1 including applying the ultrasonic waves as a single pulse.

5. The method of claim 1 including equalizing the ultrasonic waves as a series of pulses.

6. The method of claim 1 including controlling the ultrasonic waves with respect to amplitude and phase.

7. The method of claim 1 including simultaneously focusing several focused beams of ultrasonic waves directed onto the subcutaneous focus.

8. The method of claim 1 wherein the magnetic field is a direct current field.

9. The method of claim 1 wherein including applying the magnetic field as a single pulse.

10. The method of claim 1 wherein including applying the magnetic field as a pulsed field.

11. The method of claim 1 including equalizing the magnetic field in phase and frequency with the ultrasonic waves in the focal region.

12. An apparatus for neuromagnetic stimulation of subcutaneous nerve tissue comprising:

means for applying a magnetic field to a region with a magnetic induction B directed toward said subcutaneous nerve tissue for stimulation of said subcutaneous nerve tissue, and ultrasonic emitter means for simultaneously directing a focused beam of ultrasonic waves at a selected frequency into the magnetic field region, said ultrasonic waves vibrating orthogonally to the direction of the magnetic field to produce a subcutaneous focus of stimulation on said subcutaneous nerve tissue said subcutaneous focus having a focal diameter of approximately 1 cm.

13. The apparatus of, claim 12 wherein the frequency of the ultrasonic waves is in a range of 0.2 to 3 MHz.

14. The apparatus of claim 12 wherein the frequency of the ultrasonic waves is in a range of 0.3 to 0.5 MHz.

15. The apparatus of claim 12 wherein a plurality of ultrasonic emitter means is provided directing focused ultrasonic waves into the magnetic field region.

* * * * *